United States Patent
Azulay et al.

(10) Patent No.: US 11,399,732 B2
(45) Date of Patent: Aug. 2, 2022

(54) RF COIL ASSEMBLY WITH A HEAD OPENING AND ISOLATION CHANNEL

(71) Applicant: Aspect Imaging Ltd., Shoham (IL)

(72) Inventors: Shmuel Azulay, Tel Aviv (IL); James William Luther, Milan (IT); Amiel Raziel Greenberg, Mazkeret Batya (IL); Ofri Vaisman, Tel Aviv (IL); Itzchak Rabinovitz, Gan Yavne (IL); Shaul Bilu, Netanya (IL); Tobi Reuveni, Ariel (IL)

(73) Assignee: Aspect Imaging Ltd., Shoham (IL)

( * ) Notice: Subject to any disclaimer, the term of this patent is extended or adjusted under 35 U.S.C. 154(b) by 422 days.

(21) Appl. No.: 15/454,572

(22) Filed: Mar. 9, 2017

(65) Prior Publication Data

US 2018/0070852 A1      Mar. 15, 2018

Related U.S. Application Data (60) Provisional application No. 62/393,147, filed on Sep. 12, 2016.

(51) Int. Cl.
    *G01R 33/34* (2006.01)
    *G01R 33/20* (2006.01)
    (Continued)

(52) U.S. Cl.
    CPC ........ *A61B 5/055* (2013.01); *G01R 33/34046* (2013.01); *A61B 2503/04* (2013.01);
    (Continued)

(58) Field of Classification Search
    CPC ... A61B 2503/04; A61B 5/0555; A61B 5/055; G01R 33/288; G01R 33/34007;
    (Continued)

(56) References Cited

U.S. PATENT DOCUMENTS

| 4,543,959 A | 10/1985 | Sepponen |
| 4,613,820 A | 9/1986 | Edelstein et al. |

(Continued)

FOREIGN PATENT DOCUMENTS

| CN | 101185383 | 5/2008 |
| CN | 201846566 | 5/2011 |

(Continued)

OTHER PUBLICATIONS

Eberich et al., Functional MRI in neonates using neonatal head coil and MR compatible incubator, NeuroImage 20 (2003) 683-692.

(Continued)

*Primary Examiner* — Unsu Jung
*Assistant Examiner* — Adreanne A. Arnold
(74) *Attorney, Agent, or Firm* — Loeb & Loeb LLP (57) ABSTRACT

Radiofrequency (RF) coil unit and a housing for the RF coil unit is provided. The RF coil unit can include a substantially annular body having a concave indent along a longitudinal direction along the substantially annular body such that when a head of the patient is inserted into an interior of the substantially annular body, at least a portion of the head of the patient is viewable and accessible from a location exterior to the substantially annular body. The housing for the RF coil unit can include a channel to receive the RF coil unit of a MRI device. The housing can enclose regions with high voltages (e.g., 1000 Volts) and/or separate these regions from patient body parts by, for example, including insulating material, thereby enhancing a safety of the patient.

8 Claims, 7 Drawing Sheets

(51) Int. Cl.
*A61B 5/055* (2006.01)
*G01R 33/28* (2006.01)
*G01R 33/36* (2006.01)

(52) U.S. Cl.
CPC ...... *G01R 33/288* (2013.01); *G01R 33/34007* (2013.01); *G01R 33/3678* (2013.01)

(58) Field of Classification Search
CPC .... G01R 33/3678; G01R 33/34; G01R 33/36; G01R 33/32
See application file for complete search history.

(56) References Cited

U.S. PATENT DOCUMENTS

| | | | |
|---|---|---|---|
| 4,651,099 A | 3/1987 | Vinegar et al. | |
| 4,875,485 A | 10/1989 | Matsutani | |
| 4,968,961 A | 11/1990 | Miyajima et al. | |
| 5,153,546 A | 10/1992 | Laskaris | |
| 5,346,022 A | 9/1994 | Krivec | |
| 5,372,137 A * | 12/1994 | Wong | A61B 5/0555 324/309 |
| 5,436,607 A | 7/1995 | Chari et al. | |
| 5,565,831 A | 10/1996 | Dorri et al. | |
| 5,883,558 A | 3/1999 | Laskaris et al. | |
| 6,128,522 A | 10/2000 | Acker et al. | |
| 6,157,278 A | 12/2000 | Katznelson et al. | |
| 6,208,142 B1 | 3/2001 | Wagshul | |
| 6,278,274 B1 | 8/2001 | Biglieri et al. | |
| 6,323,647 B1 | 11/2001 | Anderson et al. | |
| 6,502,042 B1 | 12/2002 | Eid et al. | |
| 6,611,702 B2 | 8/2003 | Rohling et al. | |
| 6,975,115 B1 | 12/2005 | Fujita et al. | |
| 7,071,692 B2 | 7/2006 | Branch et al. | |
| 7,274,192 B2 | 9/2007 | Havens | |
| 7,378,848 B2 | 5/2008 | Gao et al. | |
| 7,399,220 B2 | 7/2008 | Krisel et al. | |
| 7,486,982 B2 | 2/2009 | Branch et al. | |
| 7,614,692 B2 | 11/2009 | Biaud | |
| 7,621,815 B2 | 11/2009 | Bosserdet, Jr. | |
| 7,760,084 B2 | 7/2010 | Jensen et al. | |
| 7,777,491 B2 | 8/2010 | Gao et al. | |
| 8,087,203 B2 | 1/2012 | Boesel et al. | |
| 8,118,488 B2 | 2/2012 | Gregerson | |
| 8,375,295 B2 | 2/2013 | Zalewski et al. | |
| 8,525,116 B2 | 9/2013 | Schulz et al. | |
| 8,555,578 B2 | 10/2013 | Hushek | |
| 8,583,294 B2 | 11/2013 | Villano et al. | |
| 8,807,084 B2 | 8/2014 | Rapoport et al. | |
| 8,851,018 B2 | 10/2014 | Rapoport et al. | |
| 8,896,310 B2 | 11/2014 | Rapoport | |
| 8,924,848 B2 | 12/2014 | Klinger | |
| 8,924,869 B2 | 12/2014 | Fellman | |
| 8,930,831 B2 | 1/2015 | Bartomeli et al. | |
| 8,984,426 B2 | 3/2015 | Endoh et al. | |
| 9,003,318 B2 | 4/2015 | Magnusson et al. | |
| 9,055,912 B2 | 6/2015 | Graumann et al. | |
| 9,599,683 B2 | 3/2017 | Armstrong et al. | |
| 2001/0038489 A1 | 11/2001 | Nakamura et al. | |
| 2002/0123681 A1 | 9/2002 | Zuk et al. | |
| 2002/0173717 A1 | 11/2002 | Rohling et al. | |
| 2003/0016518 A1 | 1/2003 | Arz | |
| 2003/0088175 A1 | 5/2003 | Branch et al. | |
| 2004/0106844 A1 | 6/2004 | Lonneker-Lammers | |
| 2004/0116799 A1 | 6/2004 | Srinivasan | |
| 2004/0127786 A1 | 7/2004 | Schmit et al. | |
| 2004/0135687 A1 | 7/2004 | Keene | |
| 2004/0147833 A1 | 7/2004 | Czipott et al. | |
| 2004/0190643 A1 | 10/2004 | Branch et al. | |
| 2004/0194989 A1 | 10/2004 | Branch et al. | |
| 2004/0196043 A1 | 10/2004 | Branch et al. | |
| 2005/0027189 A1 | 2/2005 | Branch et al. | |
| 2005/0242817 A1 | 11/2005 | Hoult | |
| 2006/0022670 A1 | 2/2006 | Kumar et al. | |
| 2006/0084857 A1 | 4/2006 | Massengill et al. | |
| 2006/0267585 A1 | 11/2006 | Havens | |
| 2006/0293590 A1 * | 12/2006 | Egan | G01R 33/34076 600/415 |
| 2007/0135704 A1 | 6/2007 | Branch et al. | |
| 2007/0191706 A1 * | 8/2007 | Calderon | A61G 7/1034 600/415 |
| 2007/0203481 A1 | 8/2007 | Gregg et al. | |
| 2007/0232894 A1 | 10/2007 | Feenan | |
| 2007/0238950 A1 | 10/2007 | Vija et al. | |
| 2008/0021317 A1 | 1/2008 | Sumanaweera | |
| 2008/0103388 A1 | 5/2008 | Maschke et al. | |
| 2008/0122441 A1 | 5/2008 | Hayakawa | |
| 2008/0171931 A1 | 6/2008 | Maschke | |
| 2008/0204028 A1 | 8/2008 | DeVries et al. | |
| 2008/0234571 A1 | 9/2008 | Hay et al. | |
| 2008/0281187 A1 | 11/2008 | Massengill et al. | |
| 2009/0209846 A1 | 8/2009 | Bammer | |
| 2009/0213997 A1 | 8/2009 | Maschke | |
| 2010/0066368 A1 | 3/2010 | Gao et al. | |
| 2010/0145358 A1 | 6/2010 | Maschke | |
| 2010/0154325 A1 | 6/2010 | Boesel et al. | |
| 2010/0219347 A1 | 9/2010 | Schulz et al. | |
| 2010/0245543 A1 | 9/2010 | Greer et al. | |
| 2011/0162652 A1 | 7/2011 | Rapoport | |
| 2011/0186049 A1 | 8/2011 | Rapoport | |
| 2011/0234347 A1 | 9/2011 | Rapoport | |
| 2011/0274238 A1 | 11/2011 | Maschke | |
| 2011/0280364 A1 | 11/2011 | Maschke | |
| 2011/0280380 A1 | 11/2011 | Maschke | |
| 2011/0282184 A1 | 11/2011 | Klingenbeck et al. | |
| 2011/0304333 A1 | 12/2011 | Rapoport | |
| 2012/0071745 A1 | 3/2012 | Rapoport | |
| 2012/0073511 A1 | 3/2012 | Rapoport et al. | |
| 2012/0077707 A1 | 3/2012 | Rapoport | |
| 2012/0119742 A1 | 5/2012 | Rapoport | |
| 2012/0126814 A1 * | 5/2012 | Fischer | G01R 33/30 324/318 |
| 2013/0079624 A1 | 3/2013 | Rapoport | |
| 2013/0109956 A1 | 5/2013 | Rapoport | |
| 2013/0150656 A1 | 6/2013 | Falk et al. | |
| 2013/0237803 A1 | 9/2013 | Rapoport | |
| 2013/0328559 A1 | 12/2013 | Rapoport | |
| 2013/0328560 A1 | 12/2013 | Rapoport | |
| 2013/0328563 A1 | 12/2013 | Rapoport | |
| 2014/0050827 A1 | 2/2014 | Rapoport | |
| 2014/0051973 A1 | 2/2014 | Rapoport et al. | |
| 2014/0051974 A1 | 2/2014 | Rapoport et al. | |
| 2014/0051976 A1 | 2/2014 | Rapoport et al. | |
| 2014/0099010 A1 | 4/2014 | Rapoport | |
| 2014/0103927 A1 | 4/2014 | Rapoport | |
| 2014/0117989 A1 | 5/2014 | Rapoport | |
| 2014/0128725 A1 | 5/2014 | Rapoport | |
| 2014/0139216 A1 | 5/2014 | Rapoport | |
| 2014/0142914 A1 | 5/2014 | Rapoport | |
| 2014/0152302 A1 | 6/2014 | Rapoport et al. | |
| 2014/0152310 A1 | 6/2014 | Rapoport | |
| 2014/0158062 A1 | 6/2014 | Rapoport et al. | |
| 2014/0230850 A1 | 8/2014 | Rapoport | |
| 2014/0257081 A1 | 9/2014 | Rapoport | |
| 2014/0266203 A1 | 9/2014 | Rapoport | |
| 2014/0300358 A1 | 10/2014 | Rapoport | |
| 2014/0354279 A1 | 12/2014 | Dumoulin et al. | |
| 2014/0354282 A1 | 12/2014 | Kusik et al. | |
| 2014/0378821 A1 | 12/2014 | Rapoport et al. | |
| 2014/0378825 A1 | 12/2014 | Rapoport et al. | |
| 2015/0005618 A1 | 1/2015 | Dumoulin | |
| 2015/0059157 A1 | 3/2015 | Rapoport | |
| 2015/0059655 A1 | 3/2015 | Rapoport | |
| 2015/0065788 A1 | 3/2015 | Rapoport | |
| 2015/0077105 A1 | 3/2015 | Rapoport et al. | |
| 2015/0137812 A1 | 5/2015 | Rapoport | |
| 2015/0141799 A1 | 5/2015 | Rapoport et al. | |
| 2015/0226817 A1 | 8/2015 | Pourrahimi | |
| 2015/0230766 A1 | 8/2015 | Wang et al. | |
| 2016/0089054 A1 | 3/2016 | Rapoport | |
| 2017/0143271 A1 | 5/2017 | Gustafsson et al. | |
| 2017/0146619 A1 | 5/2017 | Strauss et al. | |
| 2017/0181912 A1 | 6/2017 | Rapoport et al. | |

(56) References Cited

U.S. PATENT DOCUMENTS

FOREIGN PATENT DOCUMENTS

| | | |
|---|---|---|
| DE | 102008009673 | 8/2009 |
| DE | 102008009674 | 8/2009 |
| DE | 102011109375 | 2/2013 |
| DE | 202013104656 | 10/2013 |
| EP | 0187691 | 7/1986 |
| EP | 2607977 | 6/2013 |
| IL | 226488 | 5/2013 |
| JP | S5961763 | 9/1984 |
| JP | 04317630 | 11/1992 |
| JP | 2007-252741 | 10/2007 |
| WO | WO1998048756 | 11/1998 |
| WO | WO2004029644 | 4/2004 |
| WO | WO2012004797 | 1/2012 |
| WO | WO2013115847 | 8/2013 |

OTHER PUBLICATIONS

International Standard, CEI IEC 60601-1-8, Second Edition, Oct. 2006, Medical electrical equipment, Part 1-8:1-166.
Saso IEC 60601-1-10, Medical electrical equipment, Part 1-10: General requirements for basic safety and essential performance, Collateral Standard: Requirements for the development of physiologic closed-loop controllers, 2008, 1-36.
International Standard, CEI IEC 60601-1, Third Edition, Dec. 2005, Medical electrical equipment, Part 1, 1-393.
International Standard, CEI IEC 60601-2-19, Edition 2.0, Feb. 2009, Medical electrical equipment—Part 2-19: Particular requirements for the basic safety and essential performance of infant incubators, 1-80.

\* cited by examiner

RF COIL ASSEMBLY WITH A HEAD OPENING AND ISOLATION CHANNEL

CROSS REFERENCE TO RELATED APPLICATIONS

This application claims priority to U.S. Provisional Application No. 62/393,147 filed on Sep. 12, 2016.

FIELD OF THE INVENTION

The present invention relates to the field of magnetic resonance imaging (MRI), and more particularly, to a RF (radiofrequency) coil assembly.

BACKGROUND OF THE INVENTION

MRI systems are becoming ever more popular in medical procedures involving medical images of patients. MRI systems can include magnets to generate a magnetic field and one or more RF coils to transmit and receive signals. In MRI systems, proximity of an RF coil to an object to be imaged (e.g., a head of a human) can effect a signal to noise ratio (SNR) of signals received by the MRI system.

Typically, the closer the RF coil is to the object to be imaged, the better the SNR of signals used to create the image. Despite this fact, RF coils are typically not positioned directly on the object because of a potential for unwanted side effects. For example, RF coils can experience electrical breakdown.

Electrical breakdown can occur in the RF coils of the MRI systems due to, for example, high voltage and/or high RF energy stored in capacitors of the RF coils. For example, some MRI systems can provide signals at voltages that can exceed 1000 Volts. Electrical breakdown can harm a subject within an MRI system by, for example, an electric shock generated due to, for example, high voltage stored in the RF coil, that can result in a fatal injury of the subject. Moreover, the RF coil can dissipate high thermal energy that can harm the subject by, for example, causing skin burns.

Therefore, it can be desirable to position an RF coil of an MRI system within a proximity to, for example, improve MRI images. It can also be desirable to maintain a distance between the RF coil and the object to be imaged to, for example, avoid unwanted side effects from the RF coil.

SUMMARY OF THE INVENTION

One aspect of the present invention provides a radiofrequency (RF) coil unit which is operable in a magnetic resonance imaging (MRI) device, the RF coil unit includes: a substantially annular body having an internal diameter, a proximal end and a distal end, the internal diameter having a value that allows the substantially annular body to be positioned within a bore of the MRI device and accommodate at least a portion of a head of patient, the proximal end having a concave indent in a longitudinal direction along the substantially annular body such that when a head of the patient is inserted into an interior of the substantially annular body via the proximal end, at least a portion of the head of the patient is viewable and accessible from a location exterior to the substantially annular body; and a RF coil formed upon an outer surface of the substantially annular body.

In some embodiments, the RF coil includes a plurality of RF coil sections arranged more densely at the side of the substantially annular body having the concave indent than at the opposite side.

In some embodiments, the at least one of the RF coil sections are curved in relation to a form of the concave indent.

In some embodiments, the RF coil sections include conductive leads arranged end-to-end along a helical path around the substantially annular body.

In some embodiments, the substantially annular body includes flexible printed circuit board (PCB) having the RF coil sections printed thereupon.

In some embodiments, edges of the rolled PCB meet at the side of the substantially annular body being opposite to the side having the concave indent.

In some embodiments, the substantially annular body includes an air gap between the edges of the rolled PCB at the side of the substantially annular body being opposite to the side having the concave indent, wherein the conductive leads on opposite edges of the rolled PCB are interconnected by a plurality of capacitors selected to provide a quadrature coil configuration to the RF coil.

In some embodiments, the concave indent provides access to tubing in a nose and/or mouth region of the patient.

In some embodiments, the MRI device to accommodate a neonate.

Another aspect of the present invention provides a housing for a RF coil unit of an MRI device, the housing includes: a first substantially annular body comprising a first diameter, a first proximal end, a first distal end; a portion projecting inward radially from the first substantially annular body; and a second substantially annular body comprising a second diameter, a second proximal end, and second distal end, the second substantially annular body positioned within the first substantially annular body and connected to the portion such that a channel is formed inside of the first substantially annular body, the channel to receive the RF coil unit of the MRI device, and wherein the first substantially annular body, the portion and the second substantially annular body are an electrically insulating material.

In some embodiments, the first proximal end further includes a concave indent in a longitudinal direction along the first substantially annular body, and the second proximal end further comprises a concave indent in the longitudinal direction along the second substantially annular body, such that when a head of the patient is inserted into an interior of the substantially annular body via the first proximal end and the second proximal end, at least a portion of the head of the patient is viewable and accessible from a location exterior to the first substantially annular body.

In some embodiments, the second substantially annular body includes a length that prevents a RF coil unit positioned within the channel from touching a head of a patient positioned within housing.

In some embodiments, the first diameter and the second diameter are based on a strength of a field to be generated by the RF coil unit to prevent electric breakdown of the housing when the RF coil unit is positioned within the channel and emitting.

In some embodiments, the first diameter and the second diameter are based on a thickness of the RF coil unit.

In some embodiments, the MRI device to accommodate a neonate.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein is for the purpose of description and should not be regarded as limiting.

Generally, a radiofrequency (RF) coil unit is provided. The RF coil unit can include a substantially annular body having a concave indent along a longitudinal direction along the substantially annular body such that when a head of the patient is inserted into an interior of the substantially annular body, at least a portion of the head of the patient is viewable and accessible from a location exterior to the substantially annular body. The RF coil units can be from a rolled printed circuit board (PCB). The RF coil unit can improve a functionality of a RF coil, for example, by configuration of RF coil sections to have predetermined cycle density in a region adjacent to the concave indent to compensate for RF sensitivity that can be reduced due to the missing area of RF coil cycles taken by the concave indent.

Generally, a housing for a RF coil unit is provided. The housing can include a channel to receive the RF coil unit of a MRI device. The RF coil housing can enclose regions with high voltages (e.g., 1000 Volts) and/or separate these regions from patient body parts by, for example, including insulating material. In some embodiments, the channel can i) enclose an edge surrounding an interior of a substantially annular body of the RF coil unit, ii) enclose a circumference of the RF coil unit and/or iii) enclose portions of RF coils within the RF coil unit, to insulate them from the patient. For example, in a neonate MRI device, the channel can separate the neonate's head region from the RF coil to, for example, enhance the neonate's safety.

Figure 1A:
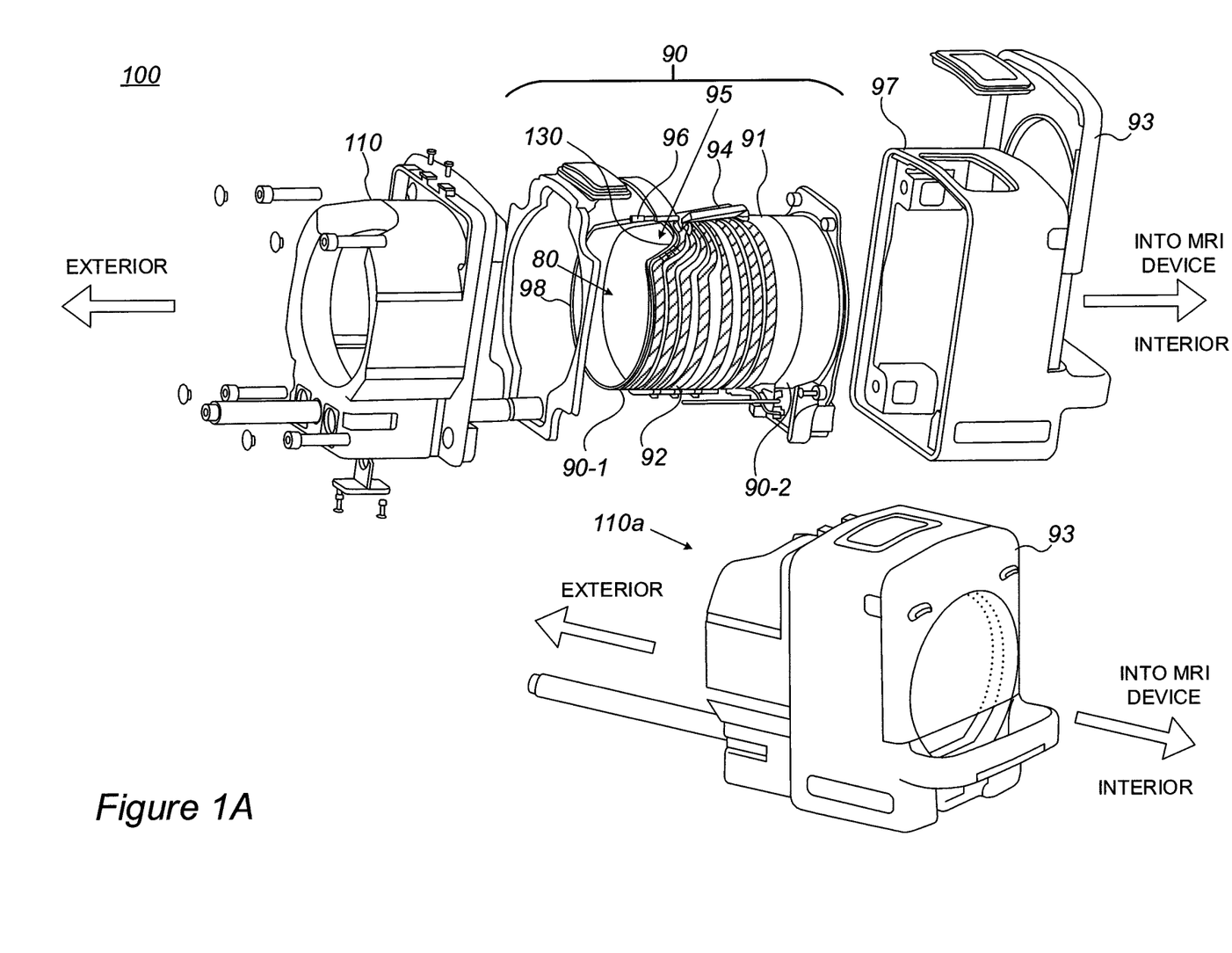
FIG. 1A is a schematic illustration of a RF coil assembly for a MRI system, according to some embodiments of the invention.
Figure 1B:
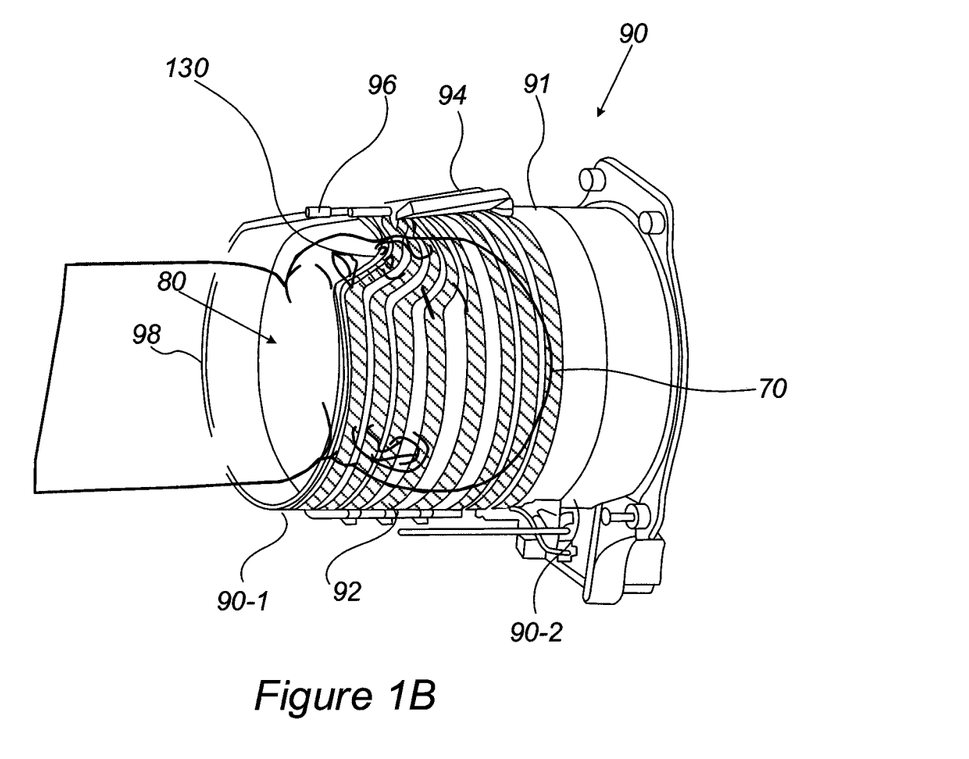
FIG. 1B is a schematic illustration of a head of a neonate positioned within a bore of a RF coil unit, according to some embodiments of the invention.
Figure 1C:
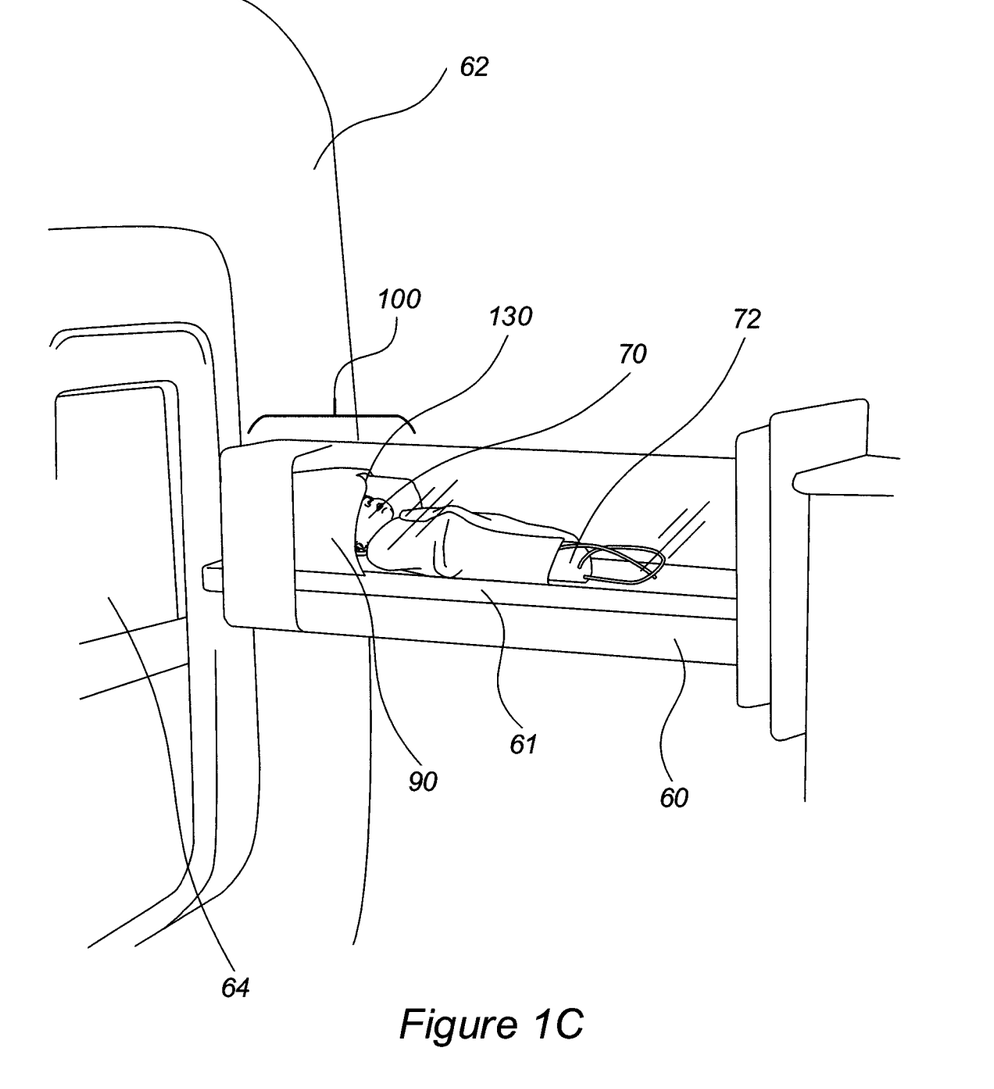
FIG. 1C is a schematic illustration of an orientation of a RF coil assembly with respect to an MRI system, according to some embodiments of the invention.

FIG. 1A is a schematic illustration of a RF coil assembly 100 for a MRI system, according to some embodiments of the invention. An assembled view 100a in FIG. 1A illustrates an example of the RF coil assembly 100 when it is assembled and/or operable in an MRI device 62 (e.g., as shown in FIG. 1C). FIG. 1B is a schematic illustration of a head 70 of a neonate positioned within a bore 80 of a RF coil unit 90, according to some embodiments of the invention. The directions interior, exterior, top and bottom indicated on FIGS. 1A-1B represent the orientation of the RF coil assembly 100 in the MRI device 62 (e.g., as shown in FIG. 1C). FIG. 1C is a schematic illustration of an orientation of a RF coil assembly 100 with respect to an MRI device 62, according to some embodiments of the invention.

The RF coil assembly 100 can include a RF coil unit 90 (e.g., as shown in FIG. 1A). The RF coil unit 90 can include a substantially annular body 91 (e.g., shell, as shown in FIGS. 1A-1B) having a proximal end 90-1, a distal end 90-2 and a bore 80 having an internal diameter. The internal diameter of the bore 80 can have a value that allows the substantially annular body 91 to be positioned within a bore 64 of the MRI device 62 and/or accommodate at least a portion of a head 70 of a patient (e.g., a neonate as shown in FIG. 1B).

The substantially annular body 91 can be cylindrical (or substantially cylindrically shaped), with optional indents and/or protrusions. The indents and/or protrusions can be formed according to desired functionality of the RF coil unit 90 and/or the MRI device 62, as explained in further detail below with respect to FIGS. 2-3.

The RF coil unit 90 can include a RF coil 92 formed upon an outer surface of the substantially annular body 91. In some embodiments, a cover 93 of the RF coil assembly 100 is opened to enable insertion of the subject, e.g., a neonate, through the bore 80, e.g., to a position 95 bordered by an indent 130 in the substantially annular body 91 of the RF coil unit 90.

The substantially annular body 91 of the RF coil unit 90 can include an edge 98 at the proximal end 90-1. The edge 98 can surround the substantially annular body 91 such that the edge 98 and/or at least a portion of the RF coil 92 can be in a close proximity to a patient or to a patient's body part. For example, at least a portion of a head 70 (e.g., of a neonate) can be introduced into the bore 80 of the RF coil unit 90 from the proximal end 90-1 such that the edge 98 and/or the RF coil 92 can be close (e.g., less than 3 mm) to a nose and/or a mouth of the neonate (e.g., as shown in FIG. 1B).

In some embodiments, the RF coil assembly 100 is movably embedded onto an incubator capsule 60 (e.g., as shown in FIG. 1C). A patient (e.g., a neonate) can be positioned onto a bed 61 of the incubator capsule 60 and/or the RF coil assembly 100 can be aligned such that the bore 80 of the RF coil unit 90 accommodates the head 70 of the patient. Incubator capsule 60 can be inserted into the bore 64 of the MRI device 62 such that the RF coil assembly 100 (e.g., including neonate's head 70) can be positioned within the interior part of MRI system 62 and, in this example, legs 72 of the neonate can be positioned within exterior portion of the MRI device 62.

Figure 2:
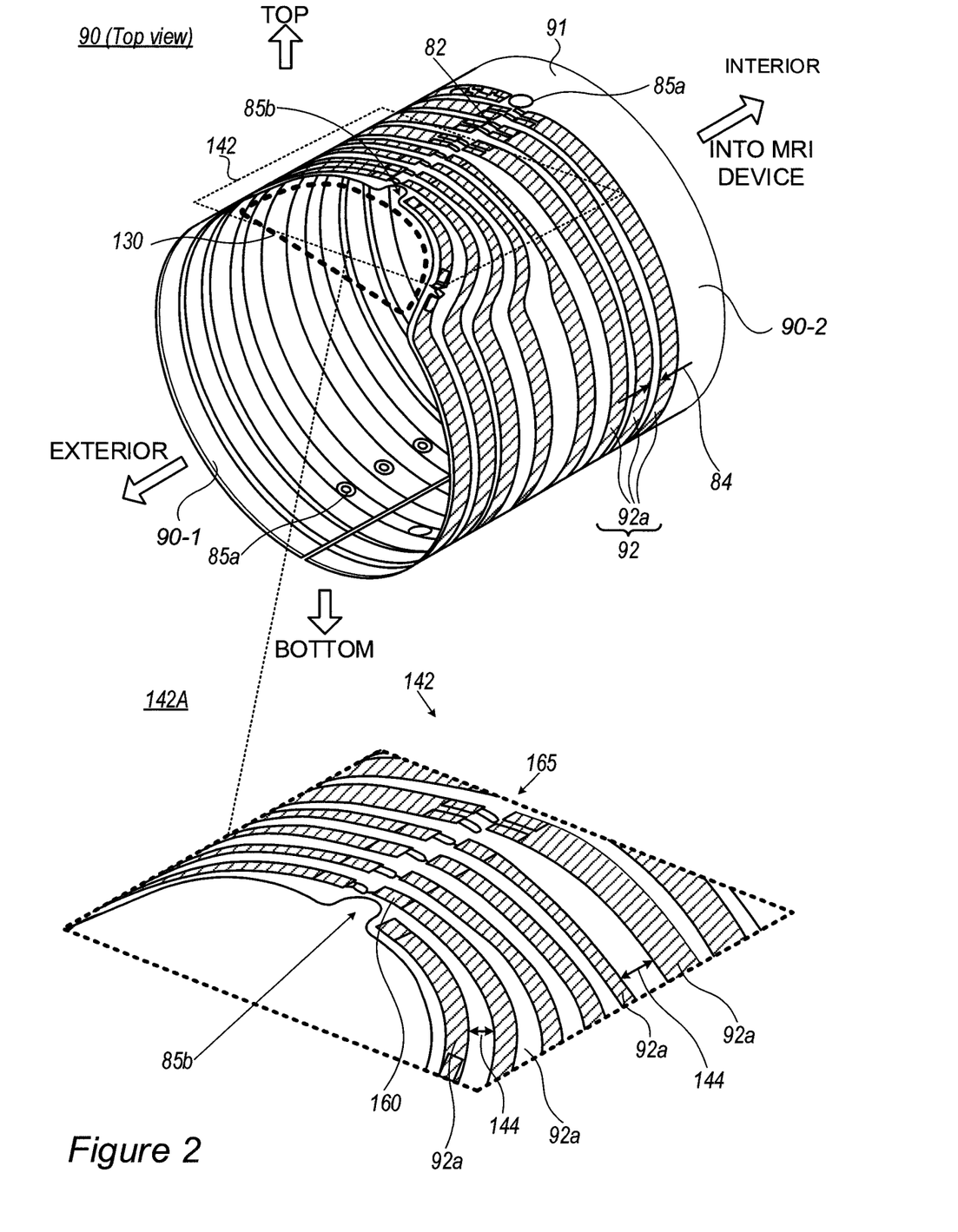
FIGS. 2 and 3 are schematic illustrations of a RF coil unit, according to some embodiments of the invention.
Figure 3:
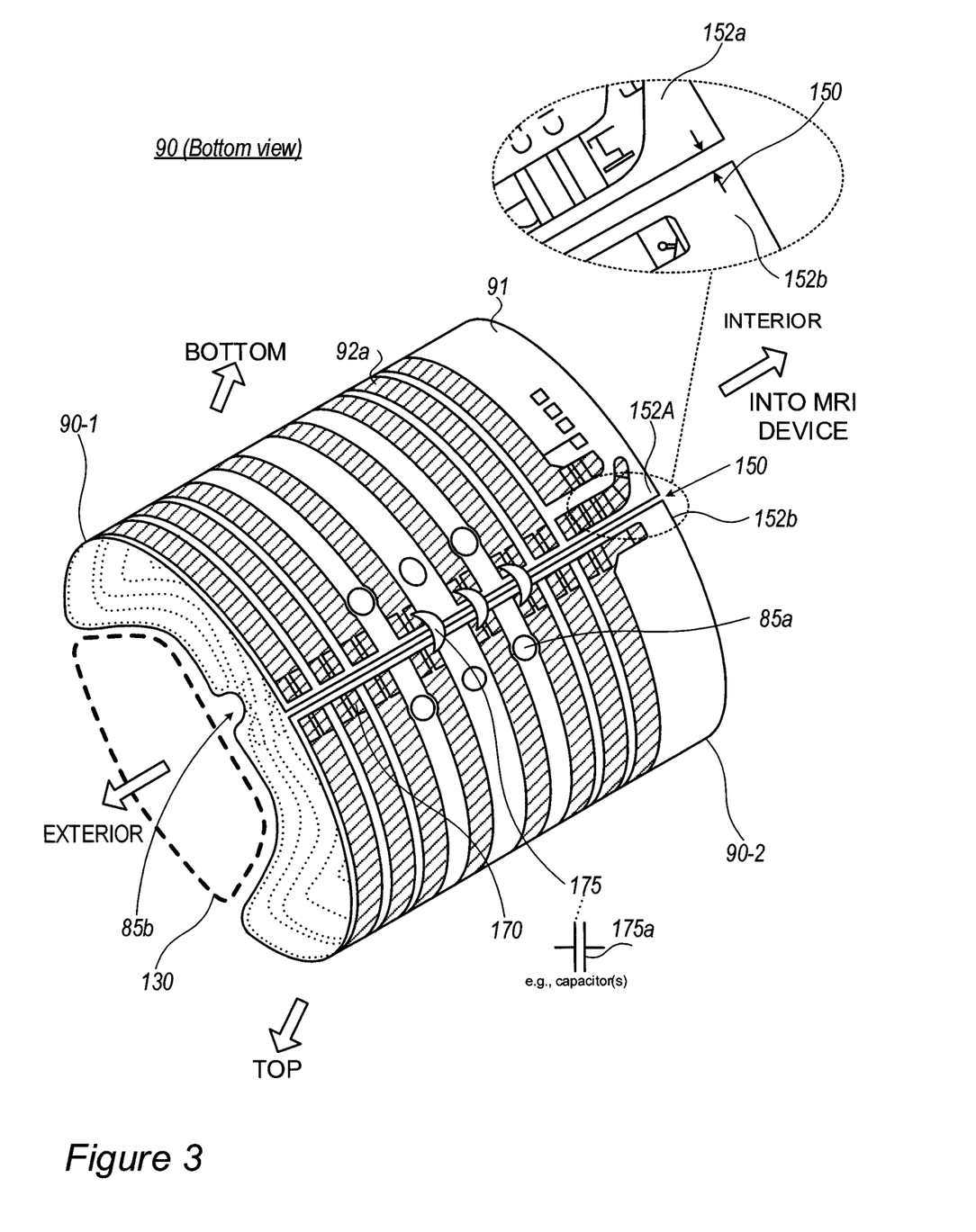

FIGS. 2 and 3 are schematic illustrations of a RF coil unit 90, according to some embodiments of the invention. FIG. 2 illustrates a top view of the RF coil unit 90 and FIG. 3 illustrates the RF coil unit 90 from a bottom view, where the top and the bottom represent the orientation of the RF coil unit 90 in the MRI device 62 (e.g., as shown in FIG. 1C).

The substantially annular body 91 of the RF coil unit 90 can include a concave indent 130 in a longitudinal direction (e.g., from the proximal end 90-1 toward the distal end 90-2) along the substantially annular body 91. The concave indent 130 can have a shape such that when the head 70 of the patient is inserted into an interior of the substantially annular body 91 via the proximal end 90-1, at least a portion of the head 70 is viewable and accessible from a location exterior (e.g., from the top) to the substantially annular body 91. In some embodiments, the concave indent 130 has a C-shape.

The concave indent 130 can allow positioning of the head 70 of a patient (e.g., a neonate) inside the RF coil unit 90 and/or the RF coil assembly 100, while, for example, life-sustaining equipment is positioned above the patient, e.g., while connected to the patient's head, thereby, for example, enhancing a safety of the patient.

In some embodiments, the concave indent 130 can enable viewing the patient's mouth and/or nose (e.g., as shown in FIG. 1B) and/or adjusting the life-sustaining equipment connections.

In various embodiments, the RF coil unit 90 and/or the RF coil assembly 100 are scaled in size for insertion of the head 70 of a human neonate, with a mouth opening for access to and observation of the neonate's mouth and equipment inserted therein, such that the head 70 occupies most of the interior of the substantially annular body 90. In various embodiments, the RF coil unit 90 and/or the RF coil assembly 100 are scaled in size for insertion of a head of a human adult and/or laboratory animals. In various embodiments, an inner diameter of the RF coil unit 90 ranges between 20 millimeters and 350 millimeters.

The RF coil 92 of the RF coil unit 90 can include a plurality of RF coil sections 92a (e.g., conductive leads) arranged end-to-end along a helical path around the substantially annular body 91. The RF coil 92 can have a larger density of the RF coil sections 92a at the side of the substantially annular body 91 having the concave indent 130 than at the opposite side. For example, in a region 142 of a top portion of the proximal end 90-1 (e.g., exterior region as shown in FIG. 2) of the substantially annular body 91 the density of the RF coil section 92a ends can be larger than at a region 82 at the distal end 90-2 (e.g., interior region as shown in FIG. 2) of the top of substantially annular body 91 (e.g., a distance 144 between consecutive RF coil sections 92a in the region 142 can be smaller than a distance 84 between the consecutive RF coil sections 92a in the region 82, as shown in FIG. 2). In some embodiments, the top segments of the RF coil sections 92a at the proximal end 90-1 can be curved in relation to a form of the concave indent 130 to allow room for the indent. A higher cycle density of the RF coil sections 92a in a region 142 can compensate for RF sensitivity loss that can be caused by the smaller area for coil cycles due to concave indent 130.

In the enlarged detail in FIG. 2, the region 142 is shown to have one or more RF coil sections 92a, which can be arranged along a substantially spiral path on the substantially annular body 91 as RF coil 92. In this embodiments, the conductive leads can be routed instead through region 142 of substantially annular body 91 adjacent to the concave indent 130, in which the density of coil cycles (e.g., cycles of the spiral path, per unit length parallel to axis of the substantially annular body 91) can be greater than cycle density in other regions (e.g., region 82) of the substantially annular body 91. A higher cycle density in region 142 adjacent to concave indent 130 can further provide an advantage of compensating for RF sensitivity that can be reduced due to a missing area of coil cycles due to the concave indent 130.

FIG. 3 schematically illustrates a bottom view of RF coil unit 90, according to some embodiments of the invention. The substantially annular body 91 can include a rolled flexible printed circuit board (PCB) having sections 92a printed thereupon. Edges 152a, 152b of the rolled PCB can be connected at the side of the substantially annular body 91 being opposite to the side having the concave indent 130 (e.g., at the bottom of the substantially annular body 91, as shown in FIG. 3), leaving an air gap 150 between straight edges 152a, 152b of the substantially annular body 91. The flexible PCB can be substantially rectangular, and rolled into substantially annular (e.g., cylindrical) shape by bringing two opposing straight edges 152a, 152b thereof to proximity, or possibly into contact.

The air gap 150 can be between opposing edges 152a, 152b, to allow dimensional tolerances of the flexible PCB and of the coil mechanics of the RF coil 92, supported by the flexible PCB. In some embodiment, using the flexible PCB can reduce costs for producing the RF coil unit 90 with the concave indent 130 and/or stabilize the RF coil unit 90. Using the flexible PCB can enable effective design of the RF coil 92 and/or the RF coil sections 92a thereof. For example, using the flexible PCB can enable isolation and/or mechanical alignment of the RF coil sections 92a, and/or can enable improvement of optimization process of RF coil's 92 performance (e.g., to achieve high uniformity and/or high signal to noise ratio (SNR) of transmitted and/or received signals).

The concave indent 130 can be located at a central position on the edge of the flexible PCB, to position the concave indent 130 at the opposite of the substantially annular body 91 with respect to air gap 150. In various embodiments, the air gap 150 has a different position with respect to the concave indent 130 (e.g., at the same portion of the substantially annular body 91 as the concave indent 130 and/or along a whole circumference of a transverse cross-section of the RF coil unit 90).

In some embodiments, RF coil sections 92a can be formed by traces on the flexible PCB, and can be narrower in region 142, to, for example, allow a higher cycle density therein. In some embodiments, spaces 144 (e.g., inter-trace distances) between the RF coil sections 92a are smaller in region 142 than spaces 84 between coil sections 92a in region 82, to, for example, allow a higher cycle density therein. Narrower RF coil sections 92a can be used in combination with narrower spaces 144 between the RF coil sections 92a. In some embodiments, a higher cycle density in region 142 can compensate for potential RF sensitivity loss by the smaller area for RF coil cycles due to the concave indent 130.

Inter-trace distances 144, 84 can be at least 3 mm wide, to, for example, reduce parasitic RF energy transfer due to capacitive coupling between traces in addition to energy transfer in the solenoid mode of the RF coil 92. The geometry of the RF coil sections 92a and of the RF coil 92 (the traces of the conductive leads) can be optimized for high performance. The optimization can include predetermining a number of RF coil sections 92a and/or predetermining values of the inter-trace distances 144, 84 in the RF coil unit 90 to, for example, achieve high uniformity and/or high signal to noise ratio (SNR) of transmitted and/or received signals, respectively.

Changes in the inter-trace distances (spaces 144, 84) along the RF coil sections 92a can be gradual, in order to, for example, reduce a risk of sharp edges of the inter-traces tearing the flexible PCB during bending. The thickness of the flexible PCB depend on a thickness that can allow bending and/or rolling the PCB with low bending resistance, e.g., on a mechanical cylinder, and reduce the risk of tearing the flexible PCB.

The RF coil 92 can include a plurality of edge contacts 170 (e.g., as shown in FIG. 3) which can be electrical connecting points of the conductive leads, near the one of opposite straight edges 152a, 152b of the flexible PCB. One, two or more edge contacts 170 can be attached to ends of each of the RF coil sections 92a (e.g., near air gap 150). The edge contacts 170 can be electrically connected to the RF coil sections 92a at the opposite edge of air gap 150 using, for example, connectors 175 (e.g., as illustrated only for three pairs of the RF coil sections 92a and can apply to all pairs). The connectors 175 can, for example, establish an electrical conductance across the air gap 150, thereby interconnecting the RF coil sections 92a into the RF coil 92. Edge contacts 170 can be any of soldering pads, mating pins, sockets and/or mating connectors. In some embodiments, connectors 175 across the air gap 150 include capacitors 175a which are soldered to edge contacts 170 (e.g., pads) and bridge conductors of edge contacts 170 terminating at opposite sides 152a, 152b of the air gap 150. Bridging the conductive leads which are interrupted at 180° intervals by capacitors 175a can form thereby a quadrature coil which can advantageously reduce the power consumption with respect to a continuous coil. Capacitors 175a can be distributed in a way that eliminates development of high voltages on any one of capacitors 175a. For example, each connector 175 can include multiple capacitors 175a arranged in series (e.g., 1, 2, or 4 capacitors per turn).

At the side of RF coil unit 90 with the concave indent 130 (e.g., at the top of RF coil 92 as shown in FIG. 2), the RF coil sections 92a can be terminated before reaching an internal gap 165 of the RF coil 92. The RF coil sections 92a can be interconnected over the internal gap 165 by, for example, internal contacts 160 (e.g., one or more internal contacts 160 per RF coil section 92a). The internal contacts 160 can be attached to ends of the conductive leads adjacent to the internal gap 165, thereby interconnecting the RF coil sections 92a into the RF coil 92. The internal gap 165 can be opposite to the air gap 150 on the substantially annular body 91. In some embodiments, each RF coil section 92a within the region 142 can be connected to opposing RF coil section 92a by one internal contact 170 while each RF coil section 92a within region 84 can be connected to opposing RF coil sections 92a by two internal contacts 170, in order to, for example, provide a higher cycle density in the region 142.

The substantially annular body 91, made e.g., from the flexible PCB, can include mounting holes 85a and mounting slots 85b for mounting the substantially annular body 91 to coil mechanics in RF coil assembly 100, e.g., by connectors such as screws (not shown). The slots 85b can simplify installation and disassembly of the RF coil 92 within the RF coil assembly 100 by enabling quick insertion or release of the substation ally annular body 91, as well as by securing the substantially annular body 91 while the remainder of screws are being fastened or unfastened.

Returning to FIGS. 1A-1B, the RF coil unit 90 can include the RF coil wire and bracket 94 which can reach very high operation voltages, while, for example, being located in close proximity to a patient body part such as the neonate's head 70 bordered by the concave indent 130 (e.g., as shown in FIG. 1B). The RF coil 92 that can be positioned in a close proximity to the inner edge 98 of the substantially annular body 91 can also reach high operation voltages in proximity to the subject, e.g., to the shoulder and/or neck of the neonate (e.g., as shown in FIG. 1B). The RF coil assembly 100 can include a housing 110 and/or additional components (not numbered, e.g., a RF coil spring stopper 96 and cover 93) which can enclose the RF coil unit 90 and/or support the operation of the MRI system in various ways, e.g., mechanically and/or electrically.

In various embodiments, the RF coil assembly 100 and/or the RF coil unit 90 is operable in a MRI device that includes permanent and/or superconducting magnets to generate a magnetic field. In various embodiments, the RF coil assembly 100 and/or the RF coil unit 90 is operable in a MRI device positioned in a dedicated RF shielded MRI room. In various embodiments, the RF coil assembly 100 and/or the RF coil unit 90 is operable in a MRI device that includes a housing that provides a RF shield to the MRI device.

Figure 4A:
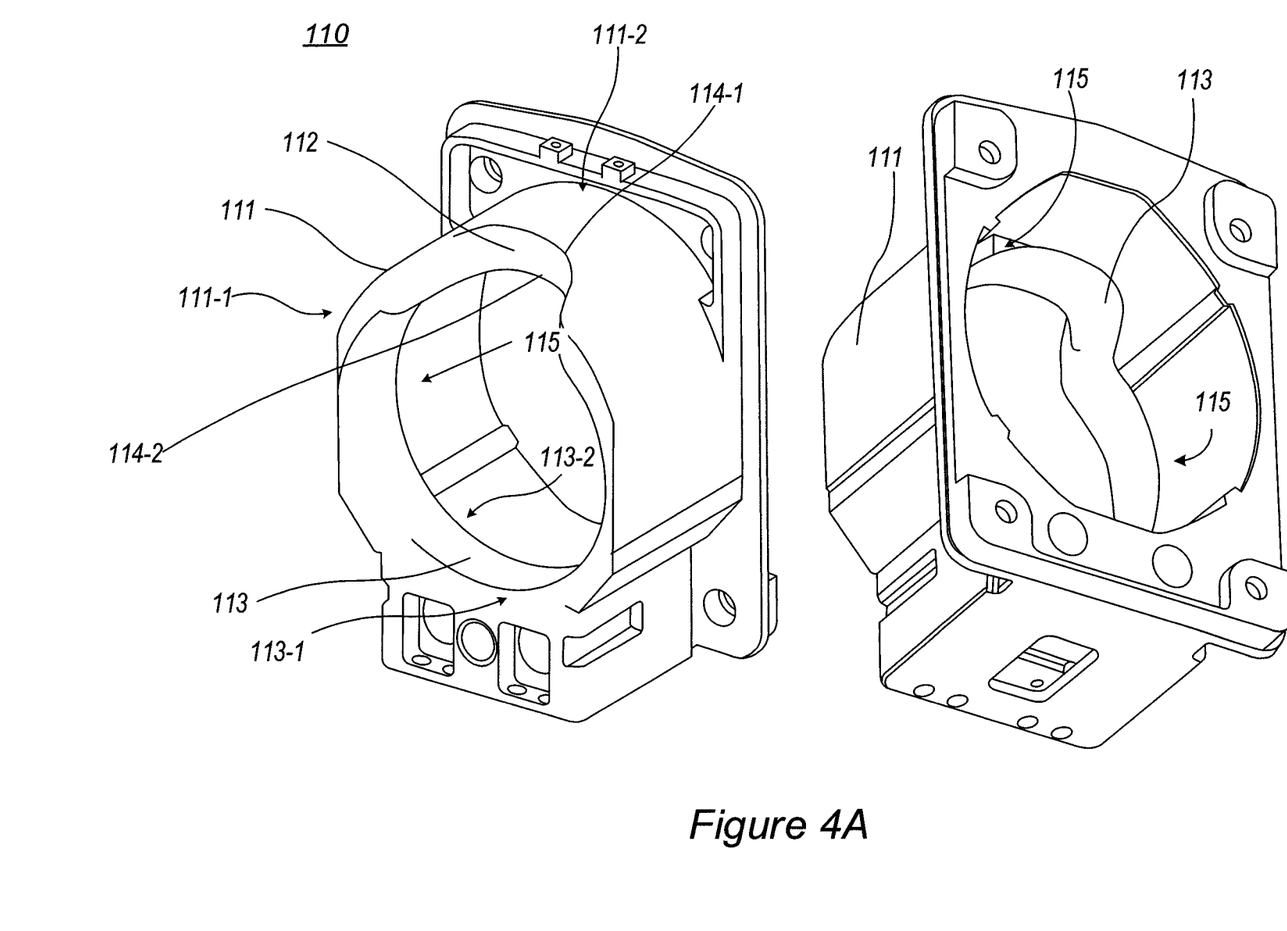
FIGS. 4A-4C are schematic illustrations of a housing of a RF coil assembly, according to some embodiments of the invention.
Figure 4B:
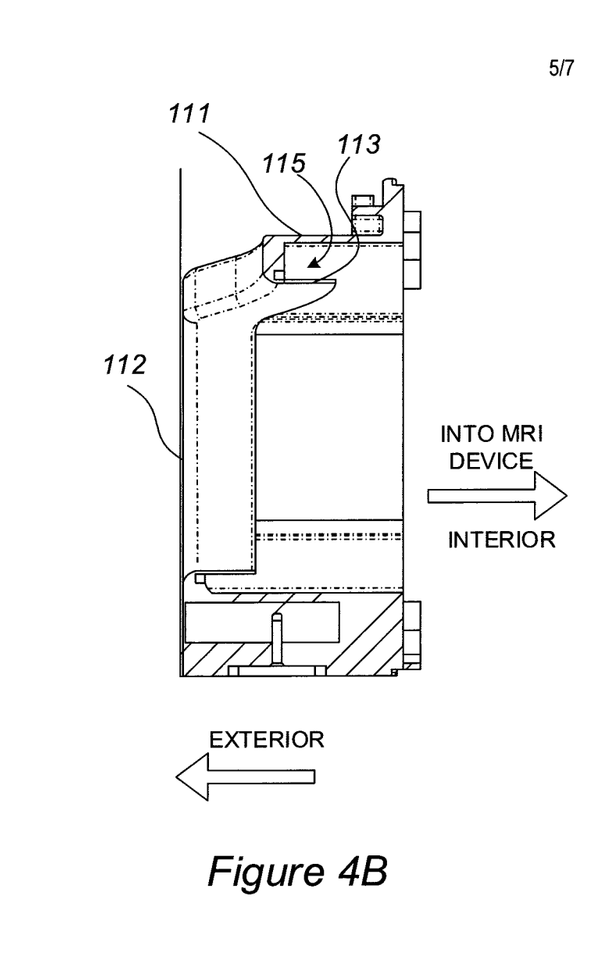
Figure 4C:
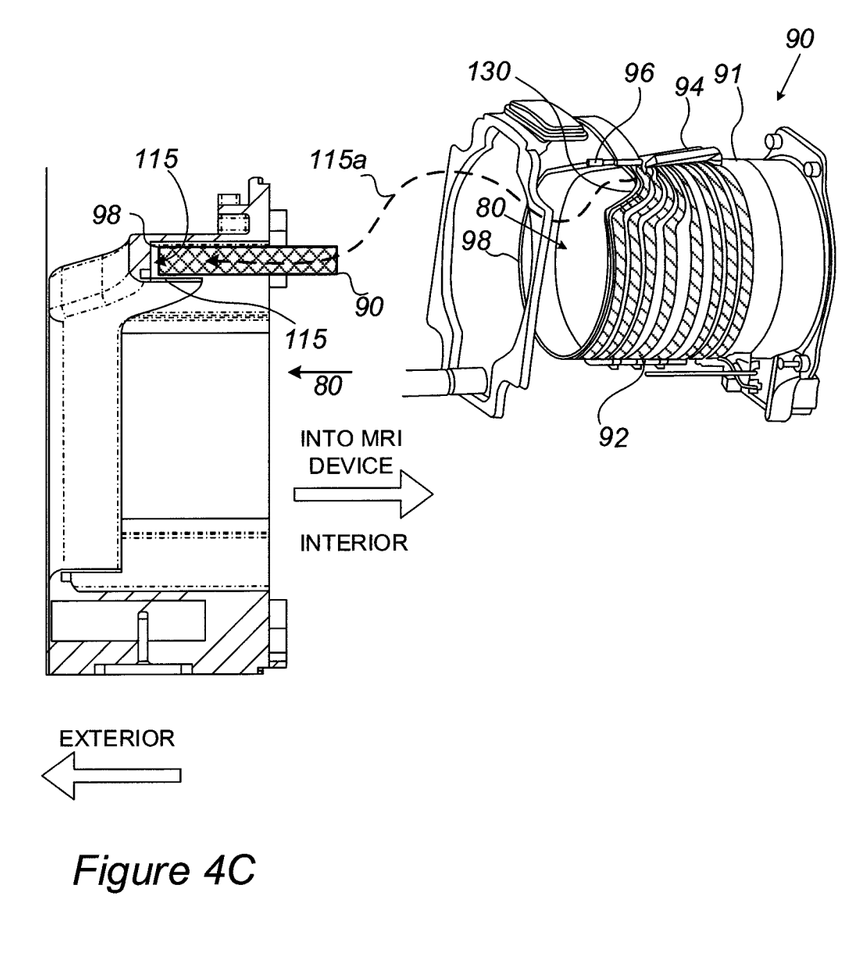

FIGS. 4A-4C are schematic illustrations of housing 110 of RF coil assembly 100, according to some embodiments of the invention. FIG. 4A presents perspective views from a proximal end 111-1 and from a distal end 111-2 of the RF coil assembly 100 (left-hand and right-hand, respectively). FIG. 4B presents a cross section view of the housing 110 and FIG. 4C presents a cross section view of the housing 110 receiving and/or enclosing the edge 98 of the RF coil unit 90.

The housing 110 can include a first substantially annular body 111 having a first diameter, a first proximal end 111-1 (e.g., exterior portion with respect to MRI device 62) and/or a first distal end 111-2 (e.g., interior portion with respect to MRI device 62). The housing 110 can include a portion 112 projecting inward radially from the first substantially annular body 111. The housing 110 can include a second substantially annular body 113 having a second diameter, a second proximal end 113-1 (e.g., exterior portion with respect to MRI device 62), and/or a second distal end 113-2 (e.g., interior portion with respect to MRI device 62). The second substantially annular body 113 can be positioned within the first substantially annular body 111 and/or connected to the portion 112 such that a channel 115 can be formed inside of the first substantially annular body 111. In various embodiments, the first substantially annular body 111, the portion 112 and/or the second substantially annular body 113 are made of an electrically insulating material, for example ULTEM 3D printed material, Acrylonitrile-Butadiene-Styrene (ABS) polymer, polycarbonate plastic, polyurethane based material and/or glass epoxy resin.

The channel 115 can receive the edge 98 of the RF coil unit 90 and/or at least a portion of the RF coil 92. In various embodiments, at least the edge 98 of the RF coil unit 90 and/or at least a portion of the RF coil 92 are insulated by the channel 115 of housing 110. In some embodiments, the channel 115 has a generally U-shape (e.g., as shown in FIGS. 4B-4C).

In various embodiments, the channel 115 extends along a portion of the circumference of the housing 110 (e.g., along a top section of the circumference with respect to MRI device 62) to insulate only a corresponding portion of the edge 98 and/or of the RF coil 92 (e.g., a top portion thereof close to the patient's face).

In some embodiments, the channel 115 is integrated with, for example, a RF coil spring stopper 96 (e.g., as shown in FIG. 1A) as part of a safety system in the RF coil assembly 100. For example, improper enclosure of the edge 98 in the channel 115 can prevent the closing of the RF coil assembly 100 and/or prevent its proper insertion into the MRI device 62. The integration can be electrical and/or mechanical.

In some embodiments, the second substantially annular body 113 includes a length that prevents the RF coil unit 90 and/or the RF coil 92 positioned within the channel 115 from touching the head 70 of the patient positioned within the housing 110. In some embodiments, the first diameter of the first substantially annular body 111 and the second diameter of the substantially annular body 113 are based on strength of a field being generated by the RF coil unit 90 to prevent electric breakdown of the housing 110 when the RF coil unit 90 is positioned within the channel 115 and emitting. In some embodiments, the first diameter and the second diameter are based on a thickness of the RF coil unit 90.

In some embodiments, the first and second proximal ends 111-1, 113-1 of first and second substantially annular bodies 111, 113 include concave indents 114-1, 114-2, respectively. The first and/or second concave indents 114-1, 114-2 can be designed in a longitudinal direction along the first and second substantially annular bodies 111, 113, respectively. In some embodiments, the head 70 of the patient is inserted into an interior of the second substantially annular body 113 via the second proximal end 113-1. The concave indents 114-1, 114-2 can thereby allow viewing and/or accessing at least a portion of the head 70 (e.g., that can be positioned within the interior of the second substantially annular body 113) from a location exterior to the first substantially annular body 111 (e.g., as shown in FIG. 1C).

One advantage of the present invention can include providing an access to medical tubing in a nose and/or mouth region of the patient (e.g., neonate as shown in FIG. 1B) through the concave indent 130 in the RF coil unit 90 of the RF coil assembly 100.

Another advantage of the present invention can include scaling of the RF coil unit 90 and/or the RF coil assembly 100 for insertion of the head 70 of a neonate, such that the head 70 occupies most of the interior of the substantially annular body 90. Such scaling can, for example, improve a quality of generated MRI images of the head 70 being imaged.

Another advantage of the present invention can include enabling MRI scanning and diagnostics of a head of prematurely born neonates, who typically have medical tubing above their head, inserted in their nose or mouth to be imaged. The present invention can provide an access to the medical tubing through the concave indent 130 in the RF coil unit 90 of the RF coil assembly 100, eliminating a need to disconnect the neonate from the medical equipment.

Another advantage of the present invention can include enhancing a safety of the neonate during operation of the MRI system 62 through, for example, an insulation of the neonate's head 70 from the RF coil 90 by, for example, the channel 115.

Elements from FIGS. 1-3 and 4A-4C can be combined in any operable combination, and the illustration of certain elements in certain figures and not in others merely serves an explanatory purpose and is non-limiting.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A RF coil assembly for a MRI device having a housing and a RF coil unit, the housing comprising:

a first substantially annular body comprising a first diameter, a first proximal end, and a first distal end;

a second substantially annular body comprising a second diameter, a second proximal end, and a second distal end, the second substantially annular body being positioned within the first substantially annular body; and a portion projecting inward radially from the first substantially annular body and connecting the first proximal end to the second proximal end such that a channel is formed between the first substantially annular body and the second substantially annular body, wherein:

the channel includes an open distal end and a closed proximal end closed by the portion, the channel being configured to receive at least a portion of the RF coil unit through the open distal end, the first substantially annular body, the portion, and the second substantially annular body are an electrically insulating material, and the first proximal end further comprises a concave indent in a longitudinal direction along the first substantially annular body, and the second proximal end further comprises a concave indent in the longitudinal direction along the second substantially annular body, the concave indents of the first and second substantially annular bodies being aligned such that when a head of the patient is inserted into an interior of the first and second substantially annular bodies via the first proximal end and the second proximal end, at least a portion of the head of the patient is viewable and accessible through the aligned concave indents, and the RF coil unit includes a substantially annular body formed from a rolled flexible printed circuit board (PCB) comprising a plurality of RF coil sections, wherein the cycle density of the RF coil sections in a first region of the PCB is greater than the cycle density of the RF coil sections in a second region of the PCB, wherein the channel is configured to receive the proximal end of the rolled flexible PCB such that when the rolled flexible PCB is so received in the channel, the first region is proximate to the concave indents and the second region is distal to the concave indents.

2. The assembly of claim 1, wherein the second substantially annular body comprises a length that prevents the RF coil unit positioned within the channel from touching a head of a patient positioned within the housing.

3. The assembly of claim 1, wherein the first diameter and the second diameter are based on a strength of a field to be generated by the RF coil unit to prevent electric breakdown of the housing when the RF coil unit is positioned within the channel and emitting.

4. The assembly of claim 1, wherein the first diameter and the second diameter are based on a thickness of the RF coil unit.

5. The assembly of claim 1, wherein a length of the first substantially annular body from the first proximal end to the first distal end is longer than a length of the second substantially annular body from the second proximal end to the second distal end.

6. The assembly of claim 1, wherein the channel extends circumferentially about at least a portion of a circumference of the housing.

7. The assembly of claim 1, wherein a portion of the channel located at the aligned concave indents is configured to receive an edge of the RF coil unit having a concave indent in the longitudinal direction.

8. The assembly of claim 1, wherein the concave indents of the housing are sized to provide access to medical tubing and/or medical equipment in a nose and/or a mouth region of the patient.

* * * * *